United States Patent
Mori et al.

[11] Patent Number: 6,104,951
[45] Date of Patent: Aug. 15, 2000

[54] IONTOPHORESIS ELECTRODE STRUCTURE

[75] Inventors: Kenji Mori; Takeshi Konno, both of Tsukuba, Japan

[73] Assignee: Hisamitsu Pharmaceutical Co., Ltd., Tosu, Japan

[21] Appl. No.: 09/029,316

[22] PCT Filed: Aug. 14, 1995

[86] PCT No.: PCT/JP95/01619

§ 371 Date: Feb. 13, 1998

§ 102(e) Date: Feb. 13, 1998

[87] PCT Pub. No.: WO97/06848

PCT Pub. Date: Feb. 27, 1997

[51] Int. Cl.[7] .................................................. A61N 1/30
[52] U.S. Cl. ........................................ 604/20; 604/501
[58] Field of Search .......................... 604/20, 21, 501, 604/22; 607/120, 129, 142, 152; 424/447, 449

[56] References Cited

U.S. PATENT DOCUMENTS

| | | | |
|---|---|---|---|
| 3,606,881 | 9/1971 | Woodson . | |
| 4,406,658 | 9/1983 | Lattin et al. | 604/20 |
| 4,764,164 | 8/1988 | Sasaki | 604/20 |
| 4,820,263 | 4/1989 | Spevak et al. | 604/20 |
| 5,006,108 | 4/1991 | LaPrade | 604/20 |
| 5,445,856 | 8/1995 | Chaloner-Gill | 428/35.9 |
| 5,466,217 | 11/1995 | Myers et al. | 604/20 |
| 5,485,569 | 1/1996 | Kirk, III et al. | 604/20 |
| 5,540,654 | 7/1996 | Riviere et al. | 604/20 |
| 5,620,580 | 4/1997 | Okabe et al. | 604/20 |
| 5,871,460 | 2/1999 | Phipps et al. | 604/20 |

FOREIGN PATENT DOCUMENTS

| | | | |
|---|---|---|---|
| 000483883 | 5/1992 | European Pat. Off. | 604/20 |
| WO 91/11215 | 8/1991 | WIPO | 604/20 |

*Primary Examiner*—Mark O. Polutta
*Assistant Examiner*—Patricia Bianco
*Attorney, Agent, or Firm*—Flynn, Thiel, Boutell & Tanis, P.C.

[57] ABSTRACT

An iontophoresis electrode structure comprising has both a polarization electrode and a non-polarization electrode, wherein both electrodes can be switched freely while the electricity is turned on. The present electrode structure makes it possible to transfer biologically active substances and drugs into a living body through the skin and the mucous membrane in a sufficient amount and safety by employing both a polarization electrode and a non-polarization electrode as iontophoresis electrodes according to a proper switch, and can transfer biologically active substances and drugs through the skin and the mucous membrane effectively without causing irritation.

8 Claims, 3 Drawing Sheets

Insulin concentration in blood after one hour

Area under the time curve of insulin concentration in blood

Accumulated insulin permeability till the 3rd hour

1. Comparative Example 2-1
2. Comparative Example 2-2
3. Comparative Example 2-3
4. Example 2-1
5. Example 2-2
6. Example 2-3

Electrode time schedule ized by an electric current to be absorbed through the skin or the mucous membrane and has been studied as an administration method instead of injections. Generally, as electrodes for iontophoresis, polarization electrodes of platinum, titanium, carbon and the like and non-polarization electrodes of silver/silver chloride and the like have been employed.

However, in the case of employing these electrodes singly, it has not been possible to transfer the biologically active substances and drugs in a sufficient amount into a living body by iontophoresis.

It is the object of the present invention to provide an electrode structure which can transfer biologically active substances and drugs into a living body effectively while causing no irritation to the skin or the mucous membrane, which has been difficult according to conventional iontophoresis techniques, and also can transfer (namely, transport) biologically active substances and drugs into a living body in a sufficient amount and safety.

DISCLOSURE OF THE INVENTION

The present invention provides an iontophoresis electrode structure having both a polarization electrode and a non-polarization electrode at the conducting element side, wherein both electrodes can be switched freely while electricity is applied thereto.

As described above, the electrode structure of the present invention has both a polarization electrode and a non-polarization electrode and is composed so that both electrodes can be switched freely while electricity is applied thereto. As materials for a polarization electrode constituting the electrode structure on the conducting element side, titanium, aluminum, iron, platinum, alloys thereof and carbon are employed, and as materials for a non-polarization electrode, silver, silver chloride, copper chloride, or materials based thereupon, for example, silver/silver chloride (silver with silver chloride adhered thereto or mixtures of both) and copper/copper chloride (copper with copper chloride adhered thereto or mixtures of both) are employed; however, they are not limited to them.

A preferred embodiment of this electrode structure 5 is composed of a polarization electrode 6 and a non-polarization electrode 7 formed integrally with an electrically insulating layer 8 (for example, a thin layer) provided between them. This electrode structure is composed, for example, as shown in FIG. 2, however, it only exemplifies one embodiment and it goes without saying that it is not limited thereto. As shown in FIG. 2, the electrode structure 5 of the present invention is composed of a polarization electrode 6 of titanium and alloys thereof, aluminum and alloys thereof, iron and alloys thereof and carbon and a non-polarization electrode 7 of silver, copper, silver chloride, copper chloride, or materials based thereupon, for example, silver/silver chloride (silver with silver chloride adhered thereto or mixtures of both) and copper/copper chloride (copper with copper chloride adhered thereto or mixtures of both) with an electrical insulating material 8, for example, polyethylene terephthalate, polyethylene, polypropylene, polyvinylidene chloride, vinyl acetate copolymer, vinyl acetate/vinyl chloride copolymer, polyamide and cellophane provided between them.

In the electrode structure 5 of the present invention, the polarization electrode 6 and the non-polarization electrode 7 are formed into a semicircular form respectively according to the circular sheet-like form in the example of FIG. 2, however, they are not limited to this embodiment and can be formed into a quadrangle, a pentagon or other proper forms with a proper thickness. In addition, the thickness and the size as a whole of the present electrode structure are selected properly according to the size and the form of diffusion cells in an iontophoresis device 1.

Moreover, for example, as shown in FIG. 1, in the electrode structure 5 of the present invention, both the polarization electrode 6 and the non-polarization electrode 7 are connected to the cathode 10 side of a power source device 2 in an iontophoresis device 1 at the conducting element side 11, and can be switched freely according to the switching operation of the power source device 2. FIG. 1 shows an embodiment for administering minus-charged biologically active substances or drugs.

In contrast, in the case of administering plus-charged biologically active substances or drugs, the switching device 3 in the iontophoresis power source device 2 is provided at the anode 14 side (plus pole side), and the electrode 5 at the conducting element side 11 is connected thereto. In this case, the electrode 12 at the non-conducting element side 13 is connected to the cathode 10 side (minus pole side) of the iontophoresis power source device.

In the case of administering biologically active substances or drugs into a living body according to iontophoresis, it is a novel technique to apply electricity by employing an electrode structure 5 comprising two kinds of electrodes as an electrode at the conducting element side 11 like the present invention. The present invention has made it possible to transfer (namely, transport) biologically active substances or drugs into a living body in a sufficient amount and safely administer biologically active substances or drugs through the skin or the mucous membrane.

In addition, as the electrode 12 at the non-conducting element side 13, namely the anode 14 side in iontophoresis employing the electrode structure on the conducting element side of the present invention, is employed a polarization electrode or a non-polarization electrode. As materials for a polarization electrode are employed, for example, platinum, titanium, aluminum, iron, alloys thereof and carbon, and as materials for a non-polarization electrode are exemplified silver, copper and zinc. As a particularly preferable combination of an electrode at the conducting element side and an electrode at the non-conducting element side can be mentioned one wherein the electrode on the conducting element side is an electrode structure comprising titanium and silver/silver chloride, and the electrode on the non-conducting element side is silver.

When administering plus-charged biologically active substances or drugs, the drugs are contained on the anode side and an electrode structure having both a polarization electrode and a non-polarization electrode at the anode side is employed. As the polarization electrode in this case is employed titanium, aluminum, iron, platinum, an alloy thereof or carbon, and as the non-polarization electrode is employed silver, copper or an alloy thereof. As a preferable combination can be mentioned titanium and silver, and carbon and silver. Moreover, in the case of administering minus-charged biologically active substances or drugs, the drugs are contained on the cathode side and an electrode structure having both a polarization electrode and a non-polarization electrode at the cathode side is employed. As the polarization electrode in this case is employed titanium, aluminum, iron, platinum, an alloy thereof or carbon, and as the non-polarization electrode is employed an electrode based on silver chloride and copper chloride. As a preferable combination can be mentioned titanium and silver/silver chloride, and carbon and silver/silver chloride.

The biologically active substances or drugs employed and used in the practice of the present invention are not particularly limited and include, for example, anaesthetic agents, analgesic agents, anorexic agents, vermicides, antiasthmatics, anticonvulsion agents, antidiarrheal agents, antimigraine agents, anti-motion-sickness agents, antivomiting agents, antitumor agents, anti-Parkinson's disease agents, antipruritics, antipyretic agents, sympathetic agents, xanthine derivatives, cardiovascular agents such as calcium transport route blocking agents, beta-blocking agents, antiarrhythmic agents, hypotensive agents, diuretic agents, vasodilators including the whole body, the coronal blood vessel, the peripheral blood vessel and the cerebral blood vessel, central nervous system excitatory state agents, drugs for coughs and colds, decongestants, diagnostic agents, hormones, sleeping drugs, immunosuppressants, muscle relaxants, parasympathetic suppressants, parasympathetic agents, nervous excitatory state agents, sedatives, tranquilizers, anti-inflammatory agents, antiarthritis agents, antispasmodics, antidepressant agents, drugs for neurotic diseases, drugs for anxiety neurosis, anaesthetic antagonists, carcinostatics, immunosuppressants, antivirus agents, antibiotics, anoretics, antiemetics, anticholine agents, antihistamine agents, hormone drugs, contraceptives and antithrombophilia agents, however, they are not limited to them.

Specific examples of the biologically active substances or drugs include insulin of peptides, calcitonins, calcitonin-connected gene peptides, vasopressin, desmopressin, protirelin (TRH), adrenocorticotropic hormone (ACTH), luteinizing hormone-releasing factor (LH-RH), growth hormone-releasing factor (GRH), nerve growth factor (NGF) and other releasing factors, angiotensin, parathyroid hormone (PTH), thyroid-stimulating hormone (TSH, thyrotropin), follicle-stimulating hormone (FSH), luteinizing hormone (LH), prolactin, serumal gonadotropic hormone, placental gonadotropic hormone (HCG), pituitary gonadotropic hormone (HMG), growth hormone, somatostatin, somatomedin, glucagon, oxytocin, gastrins, secretin, endorphin, enkephalin, endoserine, cholestquinin, neurotensin, interferon, interleukin, transferrin, erythropoietin, superoxide dismutase (SOD), granulocyte stimulating factor (G-CSF), vasoactive intestinal polypeptide (VIP), muramyl dipeptide, corticotropin, urogastrone and human atrial natriuretic peptide (h-ANP), however, they are not limited to them.

PREFERRED EMBODIMENTS FOR PERFORMING THE INVENTION

Figure 1:
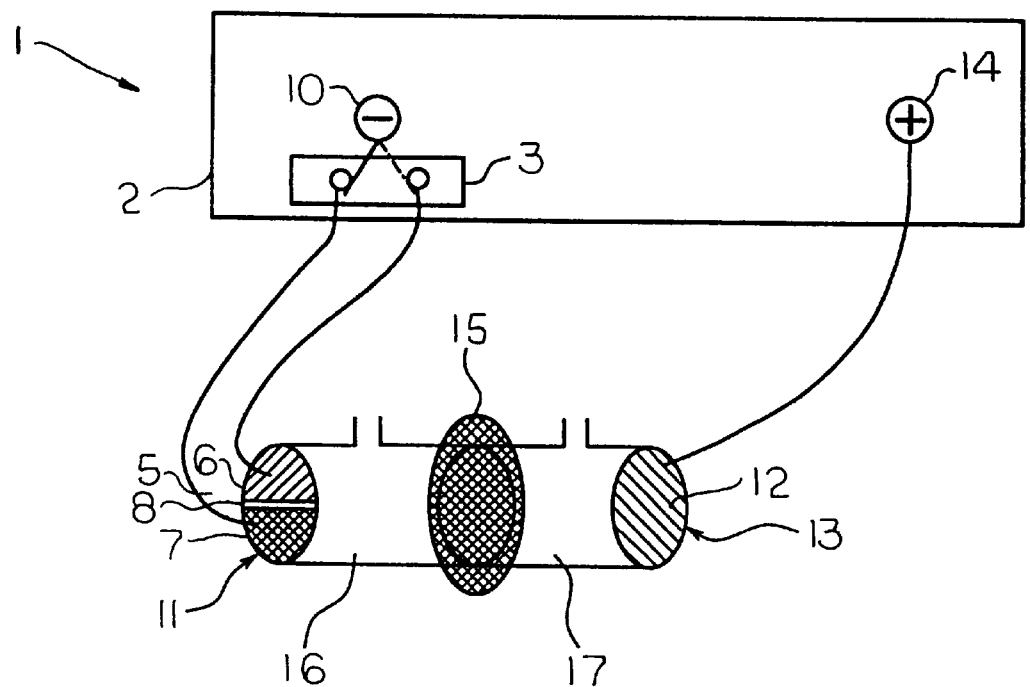
FIG. 1 is a schematic view showing an embodiment of an iontophoresis test device employing an iontophoresis electrode structure according to the present invention.

Hereunder, the present invention will be described in detail. First of all, the outlines of Test Examples (Examples) will be described, and then these Test Examples (Examples) will be described more specifically. As a test device for use was employed an iontophoresis device 1 as shown in FIG. 1.

TEST EXAMPLE 1

In Test Example 1, the back of a rat (a SD-strain rat: 250 g) was fixed, a diffusion cell was set thereon, and an insulin solution was administered thereto (amount of administration: 25 IU). At the non-conducting element side 13 directly connected to said back part, a sodium chloride-containing PVA gel formed integrally together with an electrode was employed. To an iontophoresis power source device 2 as shown in FIG. 1, an electrode 5 at the conducting element side 11 was connected to the cathode 10, and an electrode 12 at the non-conducting element side 13 was connected to the anode 14.

Figure 2:
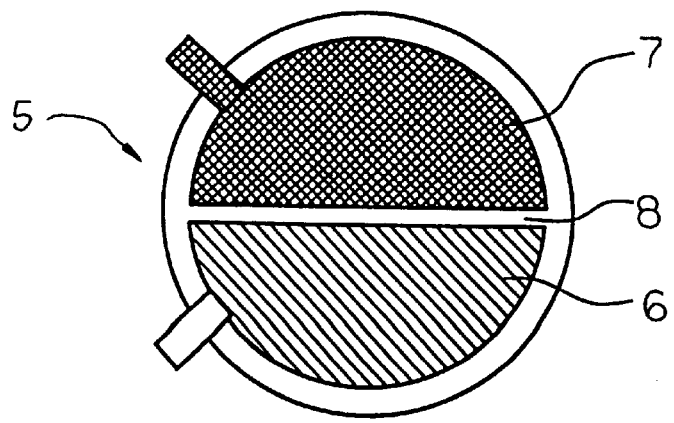
FIG. 2 is a schematic view showing an embodiment of an iontophoresis electrode structure according to the present invention at the conducting element side.

As the electrode 5 at the conducting element side 11 (cathode) in Examples was employed an electrode structure comprising a titanium electrode 6 and a silver/silver chloride electrode 7 with polyethylene terephthalate 8 provided between them according to the constitution as shown in FIG. 2, and as the electrode 12 at the non-conducting element side 13 (anode) was employed a silver electrode. On the other hand, as both the electrode at the conducting element side (cathode) and the electrode at the non-conducting element side (anode) in the Comparative Examples were employed those to be described below.

In the present test, blood was collected from the rat to the fourth hour after turning on the electricity, the insulin concentration in the blood was measured, and Example 1-1, Comparative Example 1-1, Comparative Example 1-2 and Comparative Example 1-3 were conducted.

EXAMPLE 1

In Example 1-1, the electricity was turned on at a voltage of 12 V for 15 minutes after the start of the test, employing a titanium electrode (namely, a titanium electrode of an electrode structure comprising a titanium electrode and silver/silver chloride) at the conducting element side and a silver electrode at the non-conducting element side. Thereafter, the electricity was turned on at a voltage of 6 V for 45 minutes, employing a silver/silver chloride electrode (namely, a silver/silver chloride electrode of an electrode structure comprising a titanium electrode and silver/silver chloride) at the conducting element side and the same silver electrode at the non-conducting element side. In this case, the insulin concentration in the blood after one hour in total was about 1000 $\mu$ IU/ml. The insulin concentration in blood—area under the time curve AUCø→4 h to the fourth hour was about 1.3 IU/ml min (see FIG. 3 and FIG. 4). No irritation was observed on the skin (see Table 1).

COMPARATIVE EXAMPLE 1

On the other hand, a silver/silver chloride electrode was employed at the conducting element side and a silver electrode was employed at the non-conducting element side in Comparative Example 1-1, platinum electrodes were employed at both the conducting element side and the non-conducting element side in Comparative Example 1-2; and titanium electrodes were employed at both the conducting element side and the non-conducting element side in Comparative Example 1-3.

In the case of employing a silver/silver chloride electrode at the conducting element side and a silver electrode at the non-conducting element side as in Comparative Example 1-1 and in the case of employing platinum electrodes at both the conducting element side and the non-conducting element side as in Comparative Example 1-2, insulin hardly permeated the skin one hour after the start of the test, and insulin in the collected blood could not be measured. In the case of turning on the electricity by only titanium electrodes at both the conducting element side and the non-conducting element side as in Comparative Example 1-3, the insulin concentration in the blood one hour after the start of the test was about 500 $\mu$ IU/ml, and the insulin concentration in the blood—area under the time curve (AUCø→4 h) to the fourth hour was about 0.5 IU/ml min. However, as a result of observing the skin after the completion of the test, stigmas recognized to be irritation were observed.

As shown above, it was possible to transfer insulin through the skin safely by employing the electrode structure comprising both a polarization electrode and a non-polarization electrode as in Example 1-1 of the present invention and employing the polarization electrode and the non-polarization electrode according to a switch with time. On the other hand, in the case of employing a non-polarization electrode or a polarization electrode singly as in Comparative Example 1-1, Comparative Example 1-2 and Comparative Example 1-3, it was difficult to transfer insulin into a living body without causing irritation to the skin.

TEST EXAMPLE 2

In Test Example 2, the cheek bags of a hamster were extirpated, and the corneum of the cheek bags was removed by means of a cellophane tape, which was used as a model film of the transmucosa. The mucous membrane was set in a diffusion cell having two chambers for a permeability test as shown in FIG. 1 as the mucous membrane 15, and an electrode at the donor side and an electrode at the receiver side were connected to the iontophoresis power source device as a cathode and an anode respectively. In this case, as the electrode at the conducting element side used in the Examples was employed an electrode structure as shown in FIG. 2. The electrode structure is composed of a titanium electrode and a silver/silver chloride electrode with polyethylene terephthalate provided between them. On the other hand, the electrode at the conducting element side used in the Comparative Examples was a single electrode without a switching device. After they were set as shown in FIG. 1, an insulin solution (insulin concentration: 60 IU) was supplied on the donor side 16, a phosphoric acid buffer solution was supplied on the receiver side 17, and Example 2-1, Example 2-2, Example 2-3, Comparative Example 2-1, Comparative Example 2-2 and Comparative Example 2-3 were conducted.

EXAMPLE 2

First of all, in Example 2-1, the electricity was turned on at a voltage of 18 V for 15 minutes after the start of the test, employing the titanium electrode in the above electrode structure at the conducting element side and a silver electrode at the non-conducting side, thereafter, the switching device of the iontophoresis power source device was changed, and the electricity was turned on at a voltage of 3 V for 2 hours 45 minutes, employing the silver/silver chloride electrode in the above electrode structure at the conducting element side and the same silver electrode at the non-conducting side. In this case, 0.7 IU of insulin per 1 cm$^2$ permeated the mucous membrane, and no irritation was observed to the mucous membrane.

In Example 2-2, the electricity was turned on at a voltage of 18 V for 15 minutes after the start of the test, employing the titanium electrode in the above electrode structure at the conducting element side and a silver electrode at the non-conducting element side, thereafter, the switching device of the iontophoresis power source device was used, and electricity was turned on at a voltage of 6 V for 2 hours 45 minutes, employing the silver chloride electrode in the above electrode structure at the conducting element side and the same silver electrode at the non-conducting side. In this case, 3 IU of insulin per 1 cm$^2$ permeated the mucous membrane in 3 hours in total, and no irritation was observed to the mucous membrane.

Figure 5:
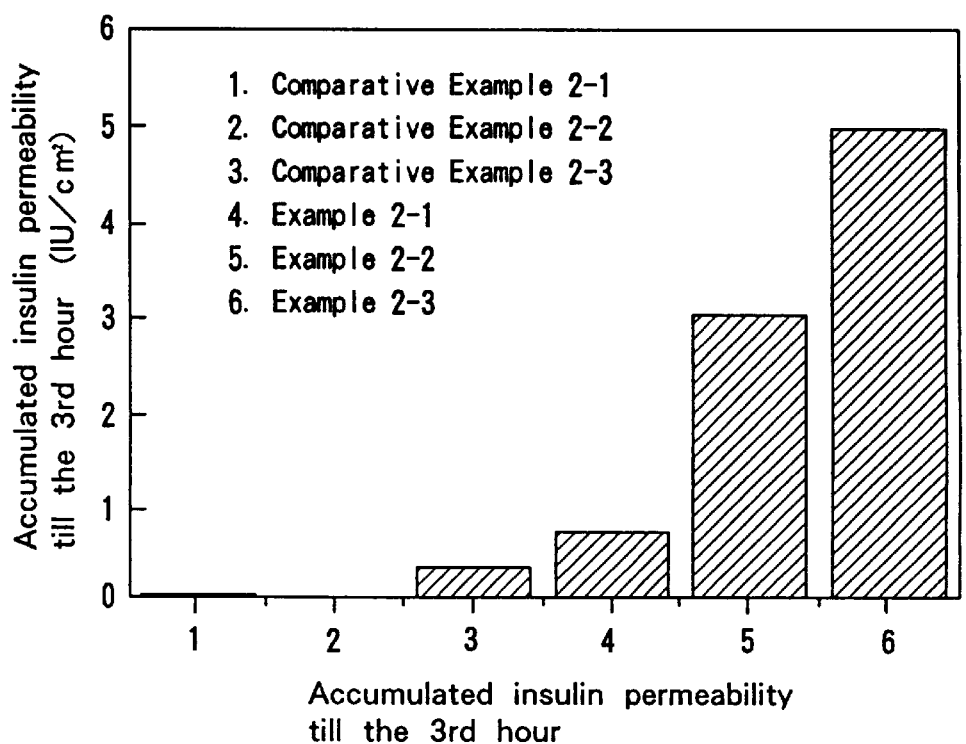
FIG. 5 is a diagram showing the mucous membrane permeability of insulin until three hours after in the Examples of the present invention.
Figure 6:
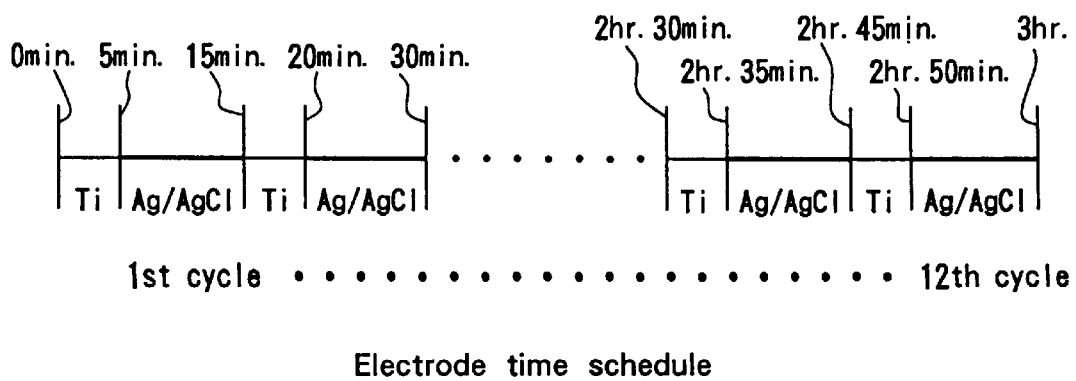
FIG. 6 is a diagram showing an electrode time schedule in Example 2-3 in Test Example 2.

Further, in Example 2-3, the electricity was turned on at a voltage of 6 V for 5 minutes after the start of the test, employing the titanium electrode in the above electrode structure at the conducting element side and a silver electrode at the non-conducting element side, thereafter, the conducting element side was switched to the silver/silver chloride electrode in the above electrode structure, and the electricity was turned on at a voltage of 6 V for 10 minutes (15 minutes in total). This was deemed as one cycle, and the electricity was turned on over 12 cycles in total, namely, over 3 hours in total. FIG. 6 shows the electrode time schedule in Example 2-3. In the case of Example 2-3, 5 IU of insulin permeated the mucous membrane in 3 hours in total, and no irritation was observed to the mucous membrane (see FIG. 5 and Table 2).

COMPARATIVE EXAMPLE 2

On the other hand, a silver/silver chloride electrode was employed at the conducting element side and a silver electrode was employed at the non-conducting element side in Comparative Example 2-1, and platinum electrodes were employed as electrodes at both the conducting element side and the non-conducting element side in Comparative Example 2-2. In both cases of Comparative Example 2-1 and Comparative Example 2-2, insulin hardly permeated the mucous membrane after 3 hours.

In Comparative Example 2-3, the electricity was turned on at a voltage of 18 V for 15 minutes after the start of the test and then at a voltage of 3 V for 2 hours and 45 minutes, employing titanium electrodes as the electrodes at both the conducting element side and the non-conducting element side. In the case of Comparative Example 2-3, about 0.3 IU of insulin per 1 cm² permeated in 3 hours, but as a result of observing the mucous membrane after the completion of the test, irritation was observed thereto.

In the present Test Example 2, it was possible to transfer insulin through the mucous membrane without causing irritation to the mucous membrane by employing the electrode structure as employed in Example 2-1, Example 2-2 and Example 2-3. On the other hand, in the case of employing a non-polarization electrode or a polarization electrode singly as in comparative Example 2-1, Comparative Example 2-2 and Comparative Example 2-3, it was not possible to allow insulin to permeate the mucous membrane without causing irritation to the mucous membrane. As described above, the present invention has made it possible to transfer biologically active substances and drugs into a living body through the skin and the mucous membrane, which was difficult according to the prior art, and, to perform the transfer without causing irritation to the skin and the mucous membrane.

Functions

Polarization electrodes comprising metals such as Ti, Al and Fe generally electrolyze water when the electricity is turned on and generate OH⁻. Thereby the slight dissolution of the tissue of the skin and the mucous membrane occurs. Substances can be transferred safely and efficiently further by performing iontophoresis administration, employing a non-polarization electrode.

Hereunder, the above Test Examples (Examples) will be described more specifically.

TEST EXAMPLE 1

The back of a rat (a SD-strain rat: 250 g) was fixed, a diffusion cell was set thereon, an insulin solution was administered thereto (amount of administration: 25 IU), and the insulin solution side was made a compartment at the conducting element side. At the non-conducting element side was applied a sodium chloride-containing PVA gel formed integrally together with an electrode. An electrode at the conducting element side was connected to the cathode of the iontophoresis power source device, and an electrode at the non-conducting element side was connected to the iontophoresis power source device as the anode. After the electricity was turned on, blood was collected from the rat with time, and the insulin concentration in the collected blood was measured.

Figure 3:
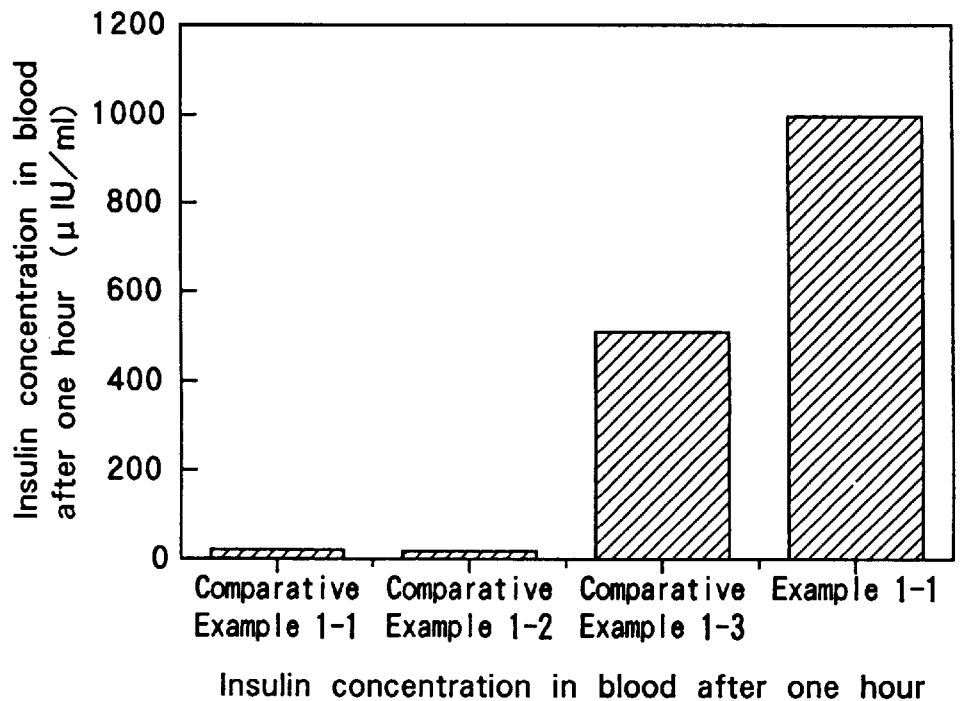
FIG. 3 is a diagram showing the insulin concentration in blood after one hour in the Examples of the present invention.
Figure 4:
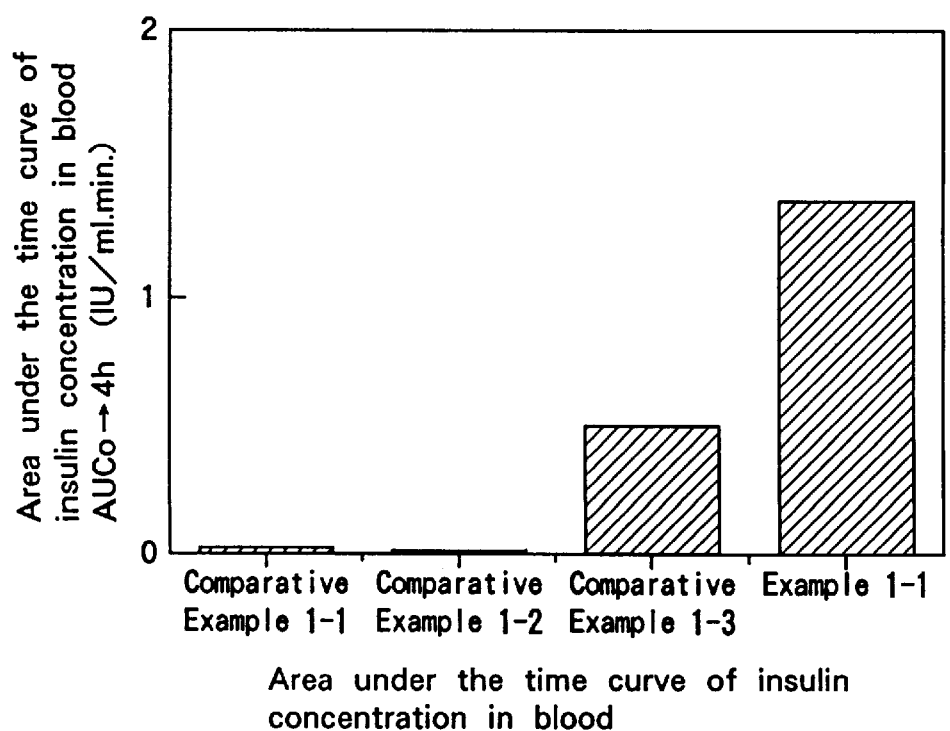
FIG. 4 is a diagram showing areas under the time curve of insulin concentration in blood in the Examples of the present invention.

After the completion of the test, the skin was observed. The electrodes with the electricity turned on and the time while the electricity was turned on in Comparative Example 1-1 to Comparative Example 1-3 and Example 1-1 were as described below. In addition, AUCø→4 h was calculated according to the trapezoid method. The results thereof are as shown in FIG. 3, FIG. 4 and the Table 1.

TABLE 1

| Skin irritation | Presence of irritation |
| --- | --- |
| Example 1-1 | Nil |
| Comparative Example 1-1 | Nil |
| Comparative Example 1-2 | Nil |
| Comparative Example 1-3 | Observed |

Example 1-1

The electricity was turned on at a voltage of 12 V for 15 minutes after the start of the test, employing a titanium electrode as the electrode at the conducting element side and a silver electrode as the electrode at the non-conducting element side, thereafter, the electricity was turned on at a voltage of 6 V for 45 minutes, employing a silver/silver chloride electrode as the electrode at the conducting element side and a silver electrode as the electrode at the non-conducting element side.

Comparative Example 1-1

The electricity was turned on at a voltage of 12 V for 15 minutes after the start of the test, employing a silver/silver chloride electrode at the conducting element side and a silver electrode at the non-conducting element side, thereafter, the electricity was turned on at a voltage of 3 V for 45 minutes.

Comparative Example 1-2

The electricity was turned on at a voltage of 12 V for 15 minutes after the start of the test, employing platinum electrodes as electrodes at both the conducting element side and the non-conducting element side, thereafter, the electricity was turned on at a voltage of 3 V for 45 minutes.

Comparative Example 1-3

The electricity was turned on at a voltage of 12 V for 15 minutes after the start of the test, employing titanium electrodes as electrodes at both the conducting element side and the non-conducting element side, thereafter, the electricity was turned on at a voltage of 3 V for 45 minutes.

TEST EXAMPLE 2

In the present Test Example, a two-chamber diffusion cell device for a permeability test as shown in FIG. 1 was employed, and as the electrode at the conducting element side in the Examples was employed an electrode structure as shown in FIG. 2. On the other hand, as the electrode at the conducting element side (cathode) and the electrode at the non-conducting element side (anode) in the Comparative Examples were employed the electrodes to be described below.

The cheek bags of a hamster (a syrian golden hamster; weight; 100 to 150 g) were extirpated, and the corneum thereof was removed by means of a cellophane tape. The film was set in the two-chamber diffusion cell for a permeability test. An insulin solution (insulin concentration: 60 IU) was applied in the compartment on the donor side (conducting element side), and a phosphoric acid buffer solution was applied in the compartment on the receiver side (non-conducting element side). The electrode at the donor side and the electrode at the receiver side were connected to the iontophoresis power source device as a cathode and an anode respectively. Besides, after the completion of the test, the mucous membrane was observed. The electrodes with the electricity turned on and the time while the electricity was turned on are as described in Example 2-1 to Example 2-3 and Comparative Example 2-1 to Comparative Example 2-3 below respectively. The results thereof are as shown in FIG. 5 and Table 2.

TABLE 2

| Mucous membrane irritation | Presence of irritation |
| --- | --- |
| Example 2-1 | Nil |
| Example 2-2 | Nil |
| Example 2-3 | Nil |
| Comparative Example 2-1 | Nil |
| Comparative Example 2-2 | Nil |
| Comparative Example 2-3 | Observed |

Example 2-1

The electricity was turned on at a voltage of 18 V for 15 minutes after the start of the test, employing a titanium electrode as the electrode at the conducting element side and a silver electrode as the electrode at the non-conducting element side, thereafter, the electricity was turned on at a voltage of 3 V for 2 hours 45 minutes, employing a silver-silver/chloride electrode as the electrode at the conducting element side and a silver electrode as the electrode at the non-conducting element side.

Example 2-2

The electricity was turned on at a voltage of 18 V for 15 minutes after the start of the test, employing a titanium electrode as the electrode on the conducting element side and a silver electrode as the electrode on the non-conducting element side, thereafter, the electricity was turned on at a voltage of 6 V for 2 hours 45 minutes, employing a silver/silver chloride electrode as the electrode at the conducting element side and a silver electrode as the electrode at the non-conducting element side.

Example 2-3

The electricity was turned on at a voltage of 6 V for 5 minutes after the start of the test, employing a titanium electrode as the electrode at the conducting element side and a silver electrode, as the electrode at the non-conducting element side, thereafter, the electricity was turned on at a voltage of 6 V for 10 minutes, employing a silver/silver chloride electrode as the electrode at the conducting element side (15 minutes in total). This was deemed as one cycle, and the electricity was turned on over 12 cycles in total, namely, over 3 hours. FIG. 6 shows the electrode time schedule in Example 2-3.

Comparative Example 2-1

The electricity was turned on at a voltage of 18 V for 15 minutes after the start of the test, employing a silver/silver chloride electrode at the conducting element side and a silver electrode at the non-conducting element side, thereafter, the electricity was turned on at a voltage of 3 V for 2 hours 45 minutes.

Comparative Example 2-2

The electricity was turned on at a voltage of 18 V for 15 minutes after the start of the test, employing platinum electrodes as electrodes at both the conducting element side and the non-conducting element side, thereafter, the electricity was turned on at a voltage of 3 V for 2 hours 45 minutes.

Comparative Example 2-3

The electricity was turned on at a voltage of 18 V for 15 minutes after the start of the test, employing titanium electrodes as electrodes at both the conducting element side and the non-conducting element side, thereafter, the electricity was turned on at a voltage of 3 V for 2 hours 45 minutes.

Effects of the Invention

The present invention makes it possible in iontophoresis to transfer biologically active substances and drugs into a living body through the skin and the mucous membrane in a sufficient amount and safety by employing an electrode structure having both a polarization electrode and a non-polarization electrode as electrodes at the conducting element side and using the polarization electrode or the non-polarization electrode according to a proper switch, and can transfer biologically active substances and drugs through the skin and the mucous membrane effectively without causing irritation.

What is claimed is:

1. An iontophoresis device comprising a power source; a first electrode assembly connected to said power source and provided at a first side of said device, said first electrode assembly being in the form of a sheet, having a circular configuration and comprising a polarization electrode and a non-polarization electrode provided in coplanar relationship with each other; a second electrode assembly connected to said power source and provided at a side of said device opposite to said first side; and a switching device for electrically switching between said polarization electrode and said non-polarization electrode.

2. The iontophoresis device of claim 1, wherein an electrically insulating material is provided between and formed integrally with the polarization electrode and the non-polarization electrode.

3. The iontophoresis device of claim 2, wherein said polarization electrode is made of titanium, said non-polarization electrode is made of silver/silver chloride, said electrically insulating material is polyethylene terephthalate and said second electrode assembly comprises an electrode made of silver.

4. The iontophoresis device of claim 1, wherein said first and second electrode assemblies are provided in parallel relationship with each other.

5. The iontophoresis device of claim 1, wherein the polarization electrode comprises a material selected from the group consisting of titanium, iron, aluminum, platinum, alloys thereof, and carbon.

6. The iontophoresis device of claim 1, wherein the non-polarization electrode comprises a material selected from the group consisting of silver, copper, silver chloride, copper chloride, and materials based thereon.

7. The iontophoresis device of claim 1, wherein said first electrode assembly is electrically connected to a cathode of the power source.

8. The iontophoresis device of claim 1, wherein said first electrode assembly is electrically connected to an anode of the power source.

* * * * *

UNITED STATES PATENT AND TRADEMARK OFFICE
CERTIFICATE OF CORRECTION

PATENT NO   : 6 104 951
DATED       : August 15, 2000
INVENTORS   : Kenji MORI et al It is certified that error appears in the above-identified patent and that said Letters Patent are hereby corrected as shown below:

On the title page: Item

[73]     change "Hisamitsu Pharmaceutical Co., Ltd."
         to ---Hisamitsu Pharmaceutical Co., Inc.---.

Signed and Sealed this

Twenty-fourth Day of April, 2001

Attest:

NICHOLAS P. GODICI

Attesting Officer

Acting Director of the United States Patent and Trademark Office